United States Patent
Horter et al.

(10) Patent No.: US 10,300,271 B2
(45) Date of Patent: May 28, 2019

(54) EMS TRAINING DEVICE, AND METHOD FOR PROTECTING AN EMS TRAINING DEVICE

(71) Applicant: Miha Bodytec GmbH, Gersthofen (DE)

(72) Inventors: Hansjürgen Horter, Oberboihingen (DE); Jürgen Decker, Emersacker (DE)

(73) Assignee: Miha Bodytec GmbH, Gersthofen (DE)

( * ) Notice: Subject to any disclaimer, the term of this patent is extended or adjusted under 35 U.S.C. 154(b) by 16 days.

(21) Appl. No.: 15/604,532

(22) Filed: May 24, 2017

(65) Prior Publication Data
US 2017/0252559 A1    Sep. 7, 2017

Related U.S. Application Data

(63) Continuation of application No. PCT/EP2015/025073, filed on Oct. 23, 2015.

(30) Foreign Application Priority Data

Dec. 16, 2014 (DE) ................. 10 2014 018 607

(51) Int. Cl.
  *A61N 1/04* (2006.01)
  *A61N 1/36* (2006.01)
(52) U.S. Cl.
  CPC ....... *A61N 1/36003* (2013.01); *A61N 1/0484* (2013.01); *A61N 1/36014* (2013.01)
(58) Field of Classification Search
  CPC ............ A61N 1/36003; A61N 1/36014; A61N 1/0484; A61N 1/0452
  See application file for complete search history.

(56) References Cited

U.S. PATENT DOCUMENTS 3,610,250 A   10/1971   Sarbacher
3,662,757 A   5/1972    Blackett
(Continued)

FOREIGN PATENT DOCUMENTS

CN    200980675    11/2007
DE    2018239      11/1970
(Continued)

OTHER PUBLICATIONS

International Search Report dated Mar. 14, 2016 of international application PCT/EP2015/025073 on which this application is based.
(Continued)

*Primary Examiner* — Joseph M Dietrich
(74) *Attorney, Agent, or Firm* — Ewers & Hasselmann PLLC

(57) ABSTRACT

An EMS training device includes an EMS stimulus generating unit for generating EMS stimuli following a specified excitation pattern with current pulses and/or an alternating current. EMS electrodes are attached to a living body in pairs for applying the EMS stimuli to the body. Line branches connect the EMS electrodes to the EMS stimulus generating unit to apply the EMS stimuli to corresponding EMS electrodes such that a current with a specified amplitude and frequency pattern is conducted through the body. To protect the EMS electrodes and/or other susceptible elements of the line branches from corrosion, the EMS training device has at least one measuring device for measuring a value of a resistance in the line branch, a comparison device for comparing the value with a target value, and at least one compensation device for compensating for a deviation of the actual value from the target value.

23 Claims, 2 Drawing Sheets

(56) References Cited

U.S. PATENT DOCUMENTS

| | | |
|---|---|---|
| 4,729,377 A | 3/1988 | Granek et al. |
| 5,285,781 A | 2/1994 | Brodard |
| 6,019,877 A | 2/2000 | Dupelle et al. |
| 6,845,272 B1 | 1/2005 | Thomsen et al. |
| 7,097,746 B1 | 8/2006 | Tziviskos et al. |
| 9,067,199 B2 | 6/2015 | Nesterenko et al. |
| 2002/0077688 A1 | 6/2002 | Kirkland |
| 2002/0077689 A1 | 6/2002 | Kirkland |
| 2002/0099320 A1 | 7/2002 | Beck |
| 2004/0009731 A1 | 1/2004 | Rabinowicz |
| 2005/0246002 A1 | 11/2005 | Martinez |
| 2009/0105795 A1 | 4/2009 | Minogue et al. |
| 2013/0113496 A1* | 5/2013 | Craige, III .............. G01R 31/04 324/511 |
| 2015/0202429 A1 | 7/2015 | Fritzsche |

FOREIGN PATENT DOCUMENTS

| | | |
|---|---|---|
| DE | 20209219 U1 | 10/2002 |
| DE | 10248235 A1 | 5/2004 |
| DE | 202004004582 U1 | 6/2004 |
| DE | 102005058850 A1 | 6/2007 |
| DE | 102007046886 A1 | 4/2009 |
| DE | 102009017179 A1 | 12/2010 |
| DE | 202011050682 U1 | 11/2011 |
| DE | 202011109226 U1 | 8/2012 |
| DE | 102012112153 A1 | 6/2014 |
| EP | 0128103 A1 | 12/1984 |
| EP | 0459945 B1 | 12/1991 |
| EP | 0965358 A2 | 12/1999 |
| EP | 2024020 A1 | 2/2009 |
| WO | 2004006700 A1 | 1/2004 |
| WO | 2005107849 A1 | 11/2005 |
| WO | 2007138071 A1 | 12/2007 |
| WO | 2011089263 A1 | 7/2011 |
| WO | 2011118918 A2 | 9/2011 |
| WO | 2014000736 A2 | 1/2014 |

OTHER PUBLICATIONS

U.S. Appl. No. 15/450,018, filed Mar. 5, 2017, Hansjürgen Horter.
U.S. Appl. No. 15/618,015, filed Jun. 8, 2017, Jürgen Decker.

\* cited by examiner

EMS TRAINING DEVICE, AND METHOD FOR PROTECTING AN EMS TRAINING DEVICE

CROSS REFERENCE TO RELATED APPLICATIONS

This application is a continuation application of international patent application PCT/EP2015/025073, filed Oct. 23, 2015, designating the United States and claiming priority from German application 10 2014 018 607.5, filed Dec. 16, 2014, and the entire content of both applications is incorporated herein by reference.

TECHNICAL FIELD

The invention relates to an EMS training device and to a method for protecting such an EMS training device.

BACKGROUND

Muscles in the living body, usually for purposes of muscle growth, are subjected in fitness studios or with personal trainers for example to electric stimuli by electric muscle stimulation (EMS), which is also partly known as electromyostimulation, in order to strengthen the muscles.

Conventional EMS electrodes to be applied to the body frequently include textile structures with incorporated metal filaments, especially silver or copper metal filaments, or pads such as polymer pads which are filled with conductive particles (e.g. carbon black). An EMS electrode is disclosed for example in the German patent application DE 10 2007 046 886 A1.

Such EMS electrodes are usually wetted before training or carried over a wetted underwear garment such as a T-shirt for example, for which purpose they are usually attached to an electrode carrier, which can be applied to the body. Whereas earlier electrode carriers frequently consisted of belt strips and leather strips, on which the electrodes were attached, the development is increasingly moving towards EMS garments, especially textile garments which carry the electrodes and can be carried by the training person themselves like a garment, i.e. as a vest, pant, stocking, armband or the like. In order to further increase the acceptance of the electric muscle stimulation (EMS), efforts are made to integrate the electrodes and the strip conductors connected to the electrodes in an increasingly better way into the EMS garment in order to thus eliminate the visible cables or at least shorten the cables leading from the EMS garment to an external control unit, and to not only eliminate the visibility of the electrodes to the greatest possible extent, but also to generally increase the wearing comfort of the EMS garment in that the EMS electrodes are formed in the most flexible and extensible manner, frequently made of textile materials. One example for such an EMS garment is disclosed in the German patent DE 10 2009 017 179 B4.

Currently, accumulator-driven EMS stimulus generation units exist, which form the EMS stimuli to be delivered to the body via the EMS electrodes and therefore can be carried directly on the EMS garment and thus on the body in an "autonomous" manner, see U.S. Pat. No. 9,067,199 and U.S. Patent Application Publication No. 2015/0202429. However, the battery power is usually insufficient in order to generate said EMS stimuli, which consist of current pulses and/or alternating current, beyond a period of time which is acceptable in training operation. For the purpose of generating said EMS stimuli, the EMS stimulus generating device usually includes an electric pulse generator for generating said EMS stimuli, as well as an electronic controller which predetermines a stimulation diagram, on the basis of which a plurality of EMS stimuli, which are distributed in respect of time and among the EMS electrodes of the EMS training device, are formed from a current drawn from a current source, which EMS stimuli consist of the current pulses and/or alternating current with values such as amplitude and frequency, which are predetermined by the controller, and with which the EMS electrodes are supplied in order to conduct a current through the body with a predetermined amplitude and frequency pattern. In this process, the EMS electrodes are usually grouped on the EMS garment in pairs, so that two EMS electrodes that are grouped to form such a pair are each connected via a line branch to the EMS stimulus generating unit, which are completed into a closed current circuit through the body on which they rest during EMS training, which current circuit leads through the body and thus through the muscles.

The line branches connecting the EMS electrodes to the EMS stimulus generating unit are formed as EMS signal cables at least between a connecting point on the EMS garment and the EMS stimulus generating unit, which EMS signal cables usually lead from the EMS stimulus generating unit, which is usually arranged remote from the training person and thus from the worn EMS garment, to the EMS electrodes or to respective connections on the EMS garment or garments. The EMS stimulus generating unit is usually housed in a control unit having a user interface, frequently in form of a control panel, and connected to the regular power grid. Such EMS training devices are produced by numerous producers and operated professionally in fitness studios by personal trainers etc., but also by private persons directly. The EMS electrodes are interconnected to the EMS stimulus generating unit, i.e. a control device, which operates for example in a frequency range of 2 to 150 Hz with a pulse width of 50 to 400 μs and an interpulse period of 0 to 10 seconds. The maximum peak value of the electrical output voltage lies at 70 to 160 V at a current intensity of approximately 10 to 20 mA, for example.

While the successes of the EMS method in muscle growth is undisputed and EMS training devices are gaining increasing interest in the audience as a result of the increasingly improved outer appearance, systematic problems are becoming more apparent due to the higher use. Consequently, inexplicable and randomly occurring failures of EMS electrodes occur in use, which leads in current EMS garments, in which the electrodes are already integrated, to the exchange of the entire EMS garment, i.e. training suit sweaters. A failure of an electrode means in this context that the EMS electrode in question no longer supplies any pulse current to the body or only an inadequate pulse current, even though no power line or contact point between the EMS electrode and the EMS stimulus generating unit, which supplies the electrode with current, seems to be broken and no defect is externally visible on the electrode.

SUMMARY

It is an object of the present invention to provide an EMS training device, with which the functionality of the EMS electrodes or EMS garments used in the EMS training device can be secured over a long period of time, and a method for protecting an EMS training device from loss of functionality of the EMS electrodes or EMS garments used in the training device during said period.

The object is achieved by providing an EMS training device including an EMS stimulation generating unit which forms from a current drawn from a current source a plurality of EMS stimuli which follows a predetermined stimulation diagram, which is distributed in respect of time and electrodes, and which includes at least one of current pulses and alternating-current with predetermined values such as amplitude and frequency. The EMS training device further includes EMS electrodes attachable to a living body for the purpose of applying the stimuli to the body and line branches, wherein each line branch connects one of the EMS electrodes in an electrically conductive manner to the EMS stimulus generating unit in order to apply said EMS electrode with EMS stimuli associated with said electrode, so that current with a predetermined amplitude and frequency pattern is conducted through the body, wherein the EMS training device includes, for corrosion protection of the EMS electrode and/or other elements susceptible thereto of at least one of the line branches, at least one measuring device in order to detect in the line branch a resistance or a quantity corresponding to the resistance as an actual value, at least one comparison device in order to compare the actual value in the line branch with a stored or determined target value, and at least one compensation device in order to compensate a deviation of the actual value from the target value in the line branch.

The object is further achieved by providing a method for protecting the EMS training device from corrosion of an EMS electrode and/or other elements susceptible to corrosion such as a push button in at least one line branch, the corrosion being caused by the operation of the EMS training device, wherein in the operation of the EMS training device, its EMS electrodes that can be attached to the living body are each electrically conductively connected to its EMS stimulus generating unit in order to form line branches, which, during the EMS training, are completed through the body to form one or several closed current circuits, wherein the line branches are associated pairwise with each other in order to form a closed current circuit extending through the body during the EMS training, a resistance or a quantity corresponding to the resistance is measured as an actual value, the actual value in the line branch is compared with a stored or determined target value, and in the event of a deviation of the actual value from the target value the deviation is compensated.

Electrostimulation is a complex electrical system. Clocked or switched-mode pulse currents are generated by the EMS stimulus generating unit and conducted via the power lines to the EMS electrodes and via the EMS electrodes into the body. In this process, the EMS electrodes are usually switched in pairs in such a way that at one point in time the first EMS electrode is supplied with the current in a pulsed manner and the second EMS electrode is not at this point in time. Upon a change of the pulse, the second EMS electrode is supplied with current in a pulsed manner and the first EMS electrode is not. Since sweat is produced on the skin surface during training, sweat, as the electrolyte, is additionally present in the current circuit of EMS stimulus generating unit (control device/pulse current feed), power line to the first EMS electrode, first EMS electrode, body, second EMS electrode, power line back to the EMS stimulus generating unit. The path of the current is even more complex with garments with several EMS electrode pairs, e.g. breast, abdomen, back, upper arms, thighs etc.

The invention is based on the recognition that, in the current circuit or circuits from the EMS stimulus generating unit to a first EMS electrode through the body of the training person via a second EMS electrode back to the EMS stimulus generating unit, different, even temporarily different, resistances can occur in the line branch leading from the EMS stimulus generating unit via the first EMS electrode to the body in comparison with the line branch leading via the second EMS electrode back to the EMS stimulus generating unit.

These resistances are caused by changing temporal conditions in the current circuit such as the differently strong contact of the respective EMS electrode on the body, locally differently strong emission of sweat on the surface of the skin, differently strong wetting of the two EMS electrodes etc., but also by systemic faults such as those at the connecting points of the EMS electrodes with EMS signal connecting cables (power lines), which are frequently formed as push buttons or crimped plugs.

These differences in resistance lead to different currents in the current feed line branch in relation to the current discharge line branch, which leads to electronic emission for example of the electrode material, the electrode/power line contact material or in the power line and thus in the end to oxidation.

This oxidation and thus corrosion occurring at different points in the electric circuit, in which the metallic material oxidises and thus corrodes at the corrosion points under electron emission, now acts itself from an electric standpoint as if an intermediate resistance were installed at the corroding points. Gradually, the oxidation and thus the increase in the resistance can go so far that the EMS electrode arranged in the affected line branch is unable to transmit the EMS stimulus required for the desired muscle contraction. This process is amplified and accelerated by sweat or the electrolytic effect of the sweat.

It is now proposed in accordance with an aspect of the invention to compensate, i.e. balance, a difference in the resistance in the feed and discharge line so that a further difference in the resistance caused by oxidation does not occur at all and/or that a difference in resistance that is still caused by an intermediate oxidation resistance is immediately compensated again. In this process, the compensation can act both in the event of a resistance indifference caused by changing temporal conditions in the circuit and also in a difference in resistance caused by a systemic error, as described above.

The EMS training device in accordance with the aspect of the invention therefore includes a compensation device configured to compensate in at least one line branch a deviation of the resistance from a target value or setpoint value. According to another aspect of the invention, in a method for operating an EMS training device, said deviation is compensated in a deviation of the resistance in at least one line branch from the target value or desired value.

In accordance with an aspect of the invention, the EMS training device further includes at least one measuring device for the protection of the EMS electrode and/or other elements of at least one of the line branches from corrosion in order to measure a resistance or a quantity corresponding to the resistance in the line branch as an actual value, which actual value is used as the starting point for a comparison between a target value and an actual value, which on the other hand forms the basis for the aforementioned compensation in the event of a deviation of the actual value from the target value or setpoint value.

In accordance with an aspect of the invention, a resistance or a quantity corresponding to the resistance is therefore measured as the actual value. Said measured quantity can be the current pulse current intensity or the current electrical resistance in the respective line branch, for example. It is also possible that potential measurement is carried out in the interpulse periods of the EMS current.

For the purpose of carrying out the comparison between the setpoint value and the actual value, the EMS training device in accordance with an aspect of the invention further includes a comparison device in order to compare the actual value with the stored or determined target value in the respective line branch. Accordingly, the actual value in the respective line branch is compared with a stored or determined target value according to the method in accordance with an aspect of the invention.

Target values stored in a memory can be used as those target values, which are compared with a current intensity and/or voltage measured in the line branch to be compensated. Preferably however, the pulse current intensity detected during the respective pulse current output in the respective line branch is compared with the pulse current intensity detected in the paired line branch. The difference of the two detected pulse current intensities then form the actual value, wherein the target value is predetermined or stored again, i.e. set to zero in identical line branches. A voltage measurement can additionally be carried out in the two line branches if necessary.

The pulse current intensity of the paired line branch is then used as the target value as the quantity corresponding to the resistance there. The comparison device can therefore set the target value for the at least one line branch to zero and determine the deviation of the actual value from the target value by a subtraction of the actual value in the respective line branch from the actual value of the other line branch, preferably from the paired line branch. This means that the comparison device does not use any fixed target value for the at least one line branch to be compensated, but detects the deviation of the actual value from the target value by a subtraction of the actual value in the respective line branch from the actual value in another line branch, preferably the paired line branch. A mean value of the actual values in several of the line branches can be determined as the target value for one of the line branches or a difference of the actual value in the respective line branch from the mean value of the actual values in the other line branches for the deviation of the actual value from the target value.

According to a further aspect of the invention, a potential difference between the respective line branch and the paired line branch is detected on the other hand as an actual value in the time segments of the interpulse periods between the EMS stimulus pulses in which no current flows, e.g. via automatic potential measurement. The potential or the potential difference between the two line branches in the circuit correspond to an electric charge, which in the ideal case assumes a predetermined or predeterminable target value, i.e. it is to be zero in identical line branches (target value). The actual value then corresponds to the detected or measured potential difference, which in the ideal case does not have any deviation from the predetermined target value, i.e. it is therefore zero in identical line branches.

The compensation can now occur in such a way, for example, that the line branch with the higher resistance is subjected to a respectively higher pulse voltage or pulse current than the other line branch in the circuit. This means that the EMS stimuli are then provided with an amplitude which is increased by the compensation current intensity or voltage. It is thus prevented that an EMS electrode or contact point emits too many electrons and is unable to refill again, i.e. it ultimately oxidises/corrodes. Therefore, the compensation device for the at least one line branch can then include a voltage and/or current intensity increasing device, via which the voltage and/or current intensity is increased in the line branch in the event of a deviation of the resistance from a desired resistance, i.e. a deviation of an actual value from a target value.

The compensation can also occur by a clocked current which is supplied in time segments of the interpulse periods between the EMS stimuli in the stimulation diagram to the line branch to be compensated, which is comparatively low in comparison with the pulses of the EMS stimuli and which is controlled for example by the aforementioned potential measurement in other time segments of the interpulse periods.

For example, the compensation current can be supplied with a current intensity of less than 2 mA and a voltage of less than 5 V over 0.1 to 0.5 seconds in a switched-mode manner in the respective time segments of the stimulus current interpulse periods that are not used for the measurement, wherein the pulse duration in current EMS training devices is approximately 0.2 to 100 ms and the duration of the interpulse periods is 0.1 to 50 ms.

The condensation device can have a voltage and/or current intensity increasing device for the at least one of the two line branches, which device is suitable for the selected type of compensation, so that either the EMS stimulus pulses are increased or the interpulse periods in between or the time segments of said interpulse periods, which are also not required for a measurement, are utilized for an increase in the voltage and/or current intensity in the respective line branch. It could also be considered to superimpose the compensation current or voltage both on the EMS stimuli and also to supply them to the time segments of the interpulse periods not used for measuring purposes.

The compensation device preferably includes a voltage and/or current intensity increasing device for one of the two line branches to be compensated, via which the voltage and/or current intensity in the line branch is increased in the event of a deviation of the measured potential difference (actual value) from the desired potential difference (target value) between the two line branches of the paired EMS electrodes, i.e. in the event of a deviation of the actual value from the target value. The switch-mode current, which is applied between the EMS stimuli and which is comparatively low in comparison with the pulses of the EMS stimuli, should be so low that it should not be perceivable by the person training with EMS and should also not disturb muscle stimulation.

Alternatively, or additionally, the compensation device for the at least one line branch can also include a protective electrode which is attached or close to the EMS electrode of said line branch, which is connected via a separate line to a current source (usually to the EMS stimulus generating unit acting as the current source) and which is supplied with current in the event of a deviation of the actual value from the target value. The protective electrode is forced to admit electrodes as a result of the current application. Said electrons then replace the electrons which would otherwise be emitted by the oxidation-endangered EMS electrode. As a result, the oxidation process of the EMS electrode is therefore stopped or at least slowed down.

The compensation currents transmitted to the protective electrode or electrodes and the associated voltages should also be so low that they are not perceived at all or as disturbing by the person training with EMS and that they do not obstruct muscle stimulation. For the purpose of compensating the increased resistance in the respective line branch, the protective electrode can advantageously be supplied in the time segments of the interpulse periods between the EMS stimuli with a switched-mode current which is comparatively low in comparison with the pulses of the EMS stimuli. Said switched-mode compensation current can also occur via a detection of the potential difference between the line branch to be compensated and the paired line branch. Alternatively, the measurement can be controlled via a detection of the potential difference between the line branch to be compensated and the line branch with the associated protective electrode. In this case, the protective electrode or the line branch with the protective electrode also acts as part of the measuring device. In both cases, the measurement is advantageously automatically carried out in the time segments of the interpulse periods which are not used for feeding with compensation current.

For example, the compensation current can be supplied with a current intensity of less than 2 mA and a voltage of less than 5 V over 0.1 to 0.5 seconds in a clocked manner in the respective time segments of the stimulus current interpulse periods that are not used for the measurement, wherein the pulse duration in current EMS training devices is approximately 0.2 to 100 ms and the duration of the interpulse periods is 0.1 to 50 ms.

In the case of the arrangement of the protective electrode directly on the EMS electrode, an insulation layer is required between the protective electrode and the EMS electrode. This allows potential measurement that is applicable for controlling. The replacement of the electrons occurs during the feed of a compensation current to the protective electrode by the humid or sweaty environment on the two electrodes.

The protective electrode(s) can consist of coated titanium or a coated titanium alloy or a noble metal. The coating can consist of mixed oxides or a noble metal or contain mixed oxides or a noble metal. It is thus achieved that the protective electrodes themselves do not oxidise or only to a lower extent.

The electrode protection method in accordance with the invention can be carried out by a technician from case to case, e.g. within the scope of a weekly or monthly maintenance of the EMS training device. He can then carry out the measurement of the actual resistance values by the measuring device, either via an existing comparison device or mentally by the comparison with the target values, and then carry out the compensation by the compensation device, i.e. an increase in the current intensity via a rotary controller for the affected line branch for example. The EMS training device preferably contains a higher-level controller however, which in the event of a response to a detected deviation of the actual value from the target value in at least one of the line branches controls or preferably feedback controls the local actual value to the local target value so that an automatic response is made to a deviation and the operational lifespan of the EMS electrodes and the EMS garments provided with said electrodes is increased to a maximum extent. It could also be considered within the scope of the invention that the high-level control unit, the measuring device, the comparison device and the compensation device are arranged in a separate unit which can be connected to the EMS training device.

It can further be considered to assign a self-consuming sacrificial anode instead of or in addition to the protective electrodes of each EMS electrode or each line branch leading from the EMS stimulus generating unit to the respective EMS electrode, i.e. to connect in an electrically conductive manner a sacrificial anode to the respective line branch instead of a non-corroding protective electrode. It could also be considered to provide a common sacrificial anode for several line branches and to connect said anode to several line branches in a conductive manner, e.g. with such which are supplied in a synchronized manner with EMS stimuli, i.e. with current pulses for example, or even in a star-shaped manner with all line branches, with respective wiring or respective switching. It might even be possible, as a result of the complex current flows in a current EMS training device with a plurality of EMS electrodes, to achieve the aforementioned corrosion protection effect without all line branches being directly in connection with a sacrificial anode.

Whereas in the selection of the material for the sacrifical anode it is necessary to use a material with a more negative standard electrode potential than the material used for the electrically conductive parts of the EMS electrode and the electrically conductive connection between the EMS stimulus generating unit and the EMS electrode, i.e. usually a material and especially a metal with a negative standard electrode potential in the electrochemical series (preferably magnesium for reasons of costs and processing, and, if possible, no non-ferrous materials for reasons of skin compatibility), one is substantially free in the selection of the place of application of the sacrificial anode as long as it is in connection with the EMS electrodes or line branches to be protected.

The EMS electrodes are advantageously arranged on one or several EMS garments such as jackets, belts, trousers, wristbands and/or leg bands, especially sewed onto said garments or knitted into said garments by a flat knitting method. At least a part of the EMS garments is advantageously formed as a textile, wherein the respective EMS garment can carry protective electrodes provided for the EMS electrode.

The EMS stimulus generating unit, the high-level control unit, the comparison device, preferably the measuring device and preferably the compensation device are advantageously arranged in a common housing which is preferably formed as a control panel and which has a connection to the power grid.

BRIEF DESCRIPTION OF THE DRAWINGS

The invention will now be described with reference to the drawings wherein.

DESCRIPTION OF EXEMPLARY EMBODIMENTS

Figure 1:
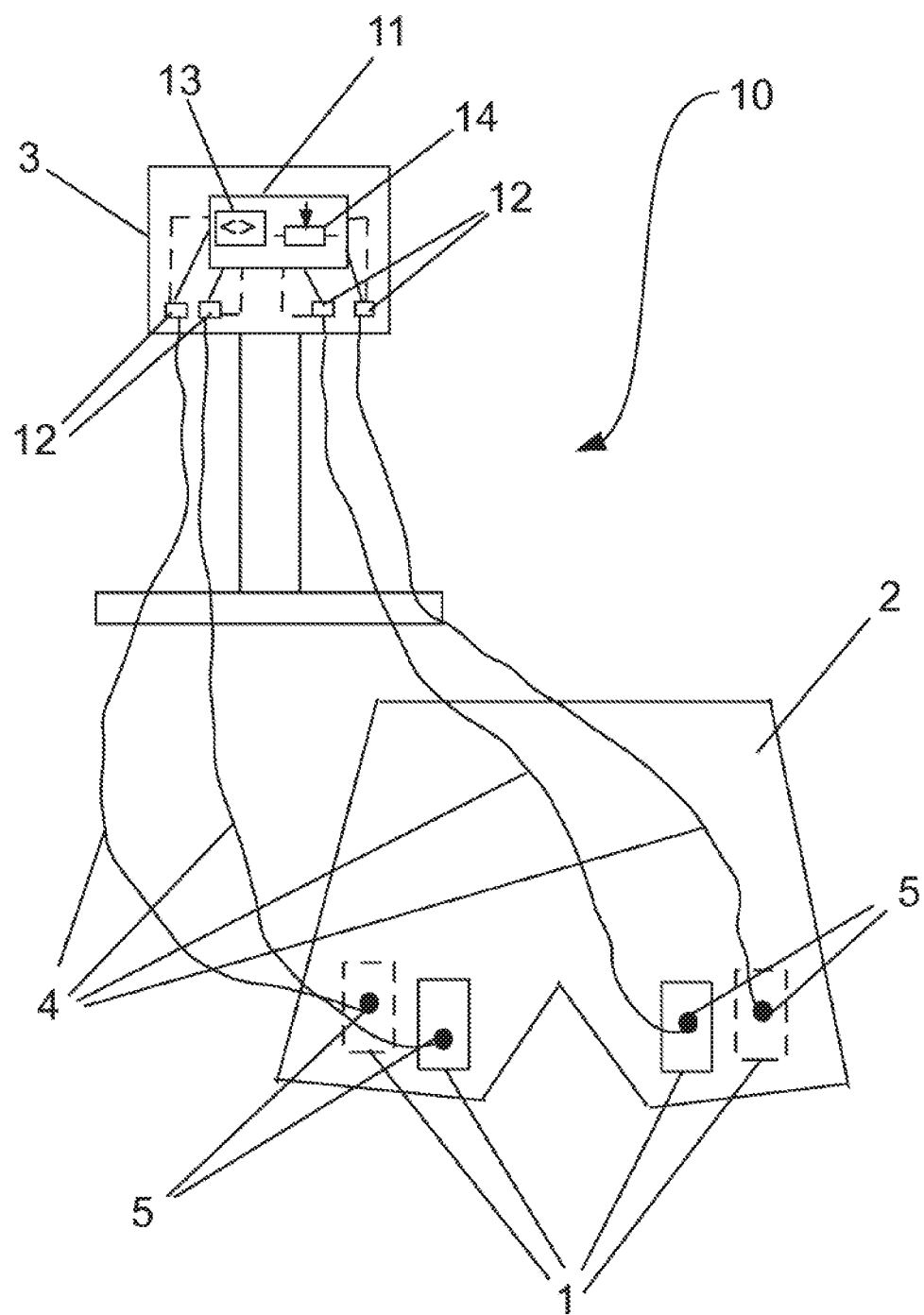
FIG. 1 shows a schematic view of an EMS training device according to a first exemplary embodiment of the invention.

FIG. 1 shows an EMS garment 2 which is arranged as a pair of shorts, which is fitted with four EMS electrodes 1 which are each grouped in two pairs, wherein each pair of electrodes is associated with a thigh, and wherein each EMS electrode 1 is connected via a signal cable or a line branch 4 to an EMS stimulus generating unit 3 which is built into a panel-like control device. The EMS garment could obviously also have a different shape such as a vest or a full body suit. It is also possible to provide a set of several EMS garments such as trousers, vest, armbands, lower leg bands. The EMS electrodes 1 can include push buttons 5, on which signal cables 4 which form the line branches leading to the EMS electrodes 1 are inserted with respective plugs. Other types of connections can be considered.

Measuring sensors forming a measuring device 12 are integrated in the control panel with the EMS stimulus generating unit 3, which forms EMS stimuli from network current according to a desired stimulation diagram, wherein each line branch 4 is associated with one of the measuring sensors, which detects an amplitude of pulse current intensity in the respective line branch 4. A higher-level controller 11 is further integrated in the control panel, which higher-level controller 11 automatically controls the local actual value to the local setpoint value in response to a detected deviation of the actual value of the pulse current intensity from a target value of the local pulse current intensity in each of the line branches 4.

For this purpose, the control unit 11 includes a comparison device 13, e.g. in form of a comparator circuit, which is known in the field and via which the comparison between the target value and the actual value is carried out, as well as a compensation device 14 configured to compensate a deviation of the actual value from the target value for each line branch 4, e.g. to increase the amplitude of the voltage pulses or current pulses in the affected line branch. The compensation device 14 can be formed separately by a regulating element in a closed regulating circuit for each line branch 4. The comparison device 13 and the compensation device 14 can be combined in a common circuit. The compensation device could also be provided in form of rotary controllers for manual readjustment, wherein in this case a display or output would have to be present for a detected deviation.

The pulse current intensity measured in the paired line branch 4 during the local pulse current output is used as the target value for the comparison between the target and the actual value, i.e. in the respective line branch which forms with the line branch 4 to be checked a closed current circuit from the EMS stimulus generating unit 3 to a first EMS electrode 1, through the thigh to a second EMS electrode 1 and back to the EMS stimulus generating unit 3. If a difference is obtained or if a differential threshold value is exceeded, a readjustment is carried out. A very low clocked current could be supplied alternatively to the measurement and the regulation of the pulse current intensity in the time segments of the interpulse periods between the EMS stimulus pulses, which clocked current is feedback controlled using automatic potential measurement in other time segments of the interpulse periods.

Figure 2:
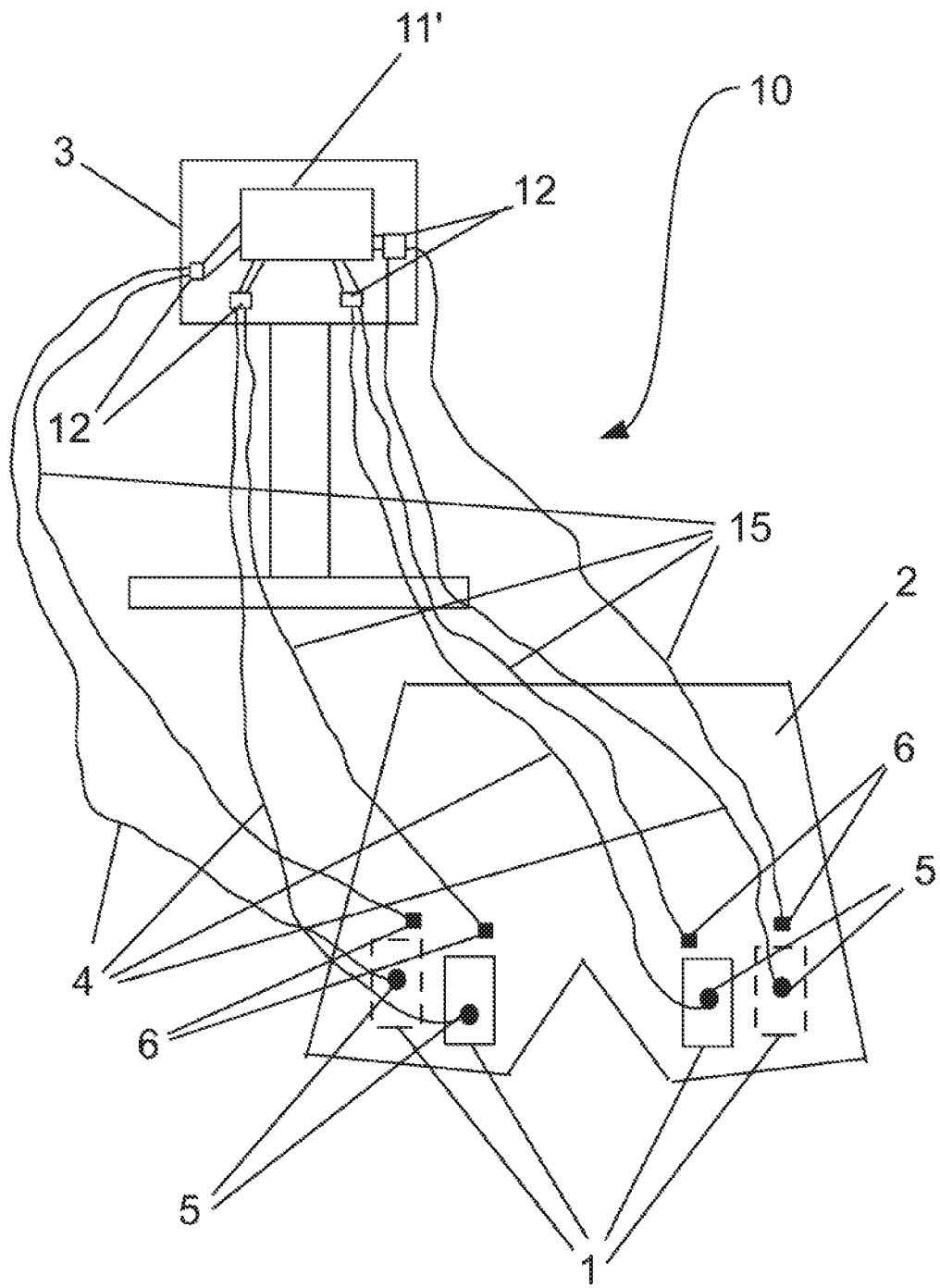
FIG. 2 shows a schematic view of an EMS training device according to a further exemplary embodiment of the invention.

A further exemplary embodiment of the invention is shown in FIG. 2. A further output on the control panel is associated with the EMS stimulus generating unit 3 and the control unit 11' in each line branch 4 leading to one of the EMS electrodes 1 as a compensation device for the compensation of a deviation of a resistance-corresponding actual value from the target value in the individual line branches, which output is connected with a line to a protective electrode 6 close to the respective EMS electrode 1. Said protective electrode 6 can consist of coated titanium or a coated titanium alloy or of a noble metal, wherein the coating can be made from mixed oxides or a noble metal. The respective protective electrode 6 is supplied by the control unit 11' in time segments of the interpulse periods with a clocked current, which is feedback controlled using automatic potential measurement in other time segments of the interpulse periods.

Said small electrodes or protective electrodes 6 shall emit electrons (by current application) without oxidising themselves and thus stop the oxidation process of the oxidation-endangered EMS electrodes 4 or reduce the speed of said oxidation to such an extent that the EMS garment 2 reaches its economic lifespan. The currents and the associated voltage must be so low that they are not perceived by the person undergoing the EMS training and do not obstruct muscle stimulation.

Deviations and modifications of the exemplary embodiments are possible without departing from the scope of the invention.

It is understood that the foregoing description is that of the exemplary embodiments of the invention and that various changes and modifications may be made thereto without departing from the spirit and scope of the invention as defined in the appended claims.

What is claimed is:

1. An electric muscle stimulation (EMS) training device for subjecting muscles in a living body to electric stimuli by EMS, the EMS training device comprising:
    an EMS stimulation generating unit which forms from a current drawn from a current source a plurality of EMS stimuli which follows a predetermined stimulation diagram and is distributed in respect of time and electrodes, and which consist of current pulses and/or alternating-current with predetermined values including a predetermined amplitude and frequency pattern;
    EMS electrodes attachable to a living body for applying the stimuli to the living body;
    line branches, wherein each line branch connects one of the EMS electrodes in an electrically conductive manner to the EMS stimulus generating unit to apply the EMS electrode with EMS stimuli associated with the EMS electrode to permit current with the predetermined amplitude and frequency pattern to be conducted through the living body;
    at least one measuring device configured to detect in one of the line branches a resistance or a quantity corresponding to the resistance as an actual value for corrosion protection of the EMS electrode and/or other elements susceptible thereto of the at least one of the line branches;
    at least one comparison device configured to compare the actual value in the one line branch with a stored or determined target value; and
    at least one compensation device configured to compensate a deviation of the actual value from the target value in the one line branch,
    wherein the EMS electrodes are pairwise associated with each other to permit the current with the predetermined amplitude and frequency pattern to be conducted through the living body in a number of current circuits respectively comprising two of the line branches, which circuits respectively comprise an associated pair of EMS electrodes.

2. The EMS training device according to claim 1, wherein the EMS training device comprises a higher-level controller, which, in response to a determination of the deviation of the actual value from the target value in the at least one line branch controls or feedback controls the actual value to the local target value.

3. The EMS training device according to claim 2, wherein the EMS training device comprises a memory in which the local target value for the at least one line branch is stored.

4. The EMS training device according to claim 1, wherein an actual value detection occurs by a subtraction of a detected actual value in the respective line branch from the detected actual value in another line branch or a mean value of detected actual values in several of the line branches.

5. The EMS training device according to claim 1, wherein by a subtraction of the actual value in the respective line branch from the actual value in the line branch which leads from the EMS stimulus generating unit to those EMS electrode which together with the EMS electrode arranged in the line branch to be compensated forms a pair in a current circuit through the living body of mutually associated EMS electrodes, and wherein the comparison device fixes the target value for the at least one line branch to be compensated to zero.

6. The EMS training device according to claim 1, wherein the actual value detection occurs by measurement of a potential difference between two line branches with paired EMS electrodes in such time segments of the interpulse periods between the EMS stimuli in a stimulation diagram, in which no compensation current feed occurs in the two line branches.

7. An The EMS training device according to claim 1, wherein the compensation device for the at least one line branch comprises a voltage and/or current intensity increasing device, via which, in response to a user input or by the controller, the voltage and/or the current intensity in the line branch is increased upon the deviation of the actual value from the target value.

8. The EMS training device according to claim 7, wherein the compensation occurs by an increase in amplitudes of the current intensity and/or the voltage of the EMS stimuli.

9. The EMS training device according to claim 7, wherein the compensation occurs in such time segments of the interpulse periods between the EMS stimuli in a stimulation diagram in which no measurement is carried out in the respective line branch to be compensated, wherein the compensation occurs by a clocked current which is fed to the respective line branch to be compensated and which is lower in relation to amplitudes of the current intensity of the EMS stimuli.

10. The EMS training device according to claim 1, wherein the compensation device for the at least one line branch comprises a protective electrode, which is attached or close to the EMS electrode of said line branch, is connected via a separate line to the current source and, in response to a user input or by the controller, is fed with current upon deviation of the actual value from the target value.

11. The EMS training device according to claim 10, wherein the actual value detection occurs by measurement of a potential difference between the respective line branch to be compensated and the protective electrode associated with its EMS electrode in such time segments of the interpulse periods between the EMS stimuli in a stimulation diagram, in which no compensation current feed occurs in the respective line branch.

12. The EMS training device according to claim 11, wherein the compensation occurs by a feedback control of a voltage and/or current intensity in the respective line branch in the event of a deviation of the potential difference from a desired potential difference between said line branch and the associated protective electrode.

13. The EMS training device according to the claim 10, wherein the protective electrode consists of a noble metal, a noble metal alloy, titanium coated with a noble metal or mixed oxides, or a titanium alloy coated with noble metal or mixed oxides.

14. The EMS training device according to claim 13, wherein an insulation layer is directly present on the associated EMS electrode between the protective electrode and the EMS electrode.

15. The EMS training device according to claim 2, wherein in each of the line branches, in response to a user input or an input by the controller, the deviation of the actual value from the target value is compensated on the basis of a measured or determined resistance or a measured or determined quantity corresponding to the resistance.

16. The EMS training device according to claim 15, wherein for each line branch at least one measuring device is provided, a separate compensation device and/or a separate comparison device.

17. The EMS training device according to claim 3, wherein the EMS electrodes (1) each comprise a flat pad which rests flexibly on the body or a textile structure section with an electrically conductive conducting layer containing metallic or metallized threads, the EMS electrodes each carry a protective electrode which is or can be connected in the electrically conductive manner to the EMS stimulus generating unit.

18. A method for protecting an electric muscle stimulation (EMS) training device for subjecting muscles in a living body to electric stimuli by the EMS from corrosion of an EMS electrode and/or other elements susceptible to corrosion including a push button in at least one line branch, which corrosion is caused by the operation of the EMS training device, wherein in the operation of the EMS training device, its EMS electrodes that can be attached to the living body are each electrically conductively connected to its EMS stimulus generating unit in order to form line branches, which, during the EMS training, are completed through the body to form one or several closed current circuits, wherein the line branches are associated pairwise with each other in order to form a closed current circuit extending through the body during the EMS training, the method comprising:
  measuring a resistance or a quantity corresponding to the resistance in one of the line branches as an actual value;
  comparing the actual value in the one of the line branches with a stored or determined target value; and
  in the event of a deviation of the actual value from the target value, compensating the deviation.

19. The method according to claim 18, wherein the EMS training device comprises:
  an EMS stimulation generating unit which forms from a current drawn from a current source a plurality of EMS stimuli which follows a predetermined stimulation diagram and is distributed in respect of time and electrodes, and which consist of current pulses and/or alternating-current with predetermined values including a predetermined amplitude and frequency pattern,
  the EMS electrodes being attachable to a living body for applying the stimuli to the body,
  line branches, wherein each line branch connects one of the EMS electrodes in an electrically conductive manner to the EMS stimulus generating unit in order to apply said EMS electrode with EMS stimuli associated with said electrode to permit current with a predetermined amplitude and frequency pattern to be conducted through the body, wherein:
  the EMS training device comprises, for corrosion protection of the EMS electrode and/or other elements susceptible thereto of at least one of the line branches, at least one measuring device in order to detect in the line branch a resistance or a quantity corresponding to the resistance as the actual value, at least one comparison device in order to compare the actual value in the line branch with a stored or determined target value, and at least one compensation device in order to compensate the deviation of the actual value from the target value in the line branch.

20. The method according to claim 18, wherein the actual value detection occurs by a subtraction of a detected actual value in the respective line branch from the detected actual value in another line branch or a mean value of detected actual values in several of the line branches.

21. The method according to claim 20, wherein the actual value detection occurs by measurement of a potential difference between two line branches with paired EMS electrodes in such time segments of the interpulse periods between EMS stimuli in a stimulation diagram, in which no compensation current feed occurs in the two line branches.

22. The method according to claim 21, wherein the compensation occurs in such time segments of the interpulse periods between the EMS stimuli in a stimulation diagram in which no measurement is carried out in the respective line branch to be compensated, and
   wherein the compensation occurs by a clocked current which is fed to the respective line branch to be compensated and which is lower in relation to amplitudes of current intensity of the EMS stimuli.

23. The method according to claim 22, wherein the compensation occurs by a feedback control of a voltage and/or current intensity in the respective line branch in the event of a deviation of the potential difference from a desired potential difference between said line branch and the associated protective electrode.

\* \* \* \* \*